United States Patent [19]

Ohtaka et al.

[11] Patent Number: 4,663,325
[45] Date of Patent: May 5, 1987

[54] 1-(2,3,4-TRI-METHOXYBENZYL)-4[BIS(4-FLUOROPHENYL)METHYL] PIPERAZINES ARE USEFUL FOR TREATING CEREBROVASCULAR DISEASE

[75] Inventors: Hiroshi Ohtaka; Toshiro Kanazawa; Keizo Ito, all of Osaka; Goro Tsukamoto, Toyonaka, all of Japan

[73] Assignee: Kanebo Ltd., Tokyo, Japan

[21] Appl. No.: 715,813

[22] Filed: Mar. 25, 1985

[30] Foreign Application Priority Data

Mar. 30, 1984 [JP] Japan ................................. 59-64464

[51] Int. Cl.⁴ .................. A61K 31/505; C07D 295/04
[52] U.S. Cl. ..................................... 514/255; 544/396
[58] Field of Search ......................... 544/396; 514/255

[56]        References Cited
        U.S. PATENT DOCUMENTS 3,868,377  2/1975  Raabe et al. ....................... 544/396

FOREIGN PATENT DOCUMENTS 133323   8/1983  European Pat. Off. ............ 544/396
1303080  9/1962  France .
M1538   11/1962  France .
705979   3/1954  United Kingdom .

OTHER PUBLICATIONS

Regnier et al, Chem. Abst., 60-2965a eq. French '080.
Graizon et al, Chem. Abst., 60-1772h eq. French M1538.
Raabe et al, Chem. Abst., 93-186413k.

Primary Examiner—Donald G. Daus
Assistant Examiner—Cecilia Shen

Attorney, Agent, or Firm—Wenderoth, Lind & Ponack

[57]            ABSTRACT

A 1-benzyl-4-benzhydrylpiperazine derivative represented by the following general formula (I)

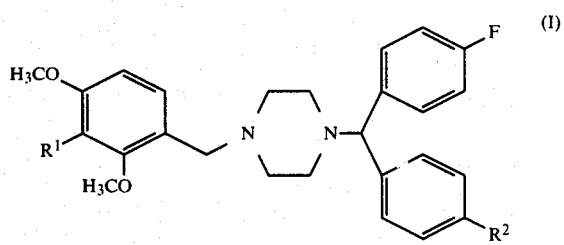

wherein
  R¹ represents a hydrogen atom or a methoxy group, and
  R² represents a hydrogen or fluorine atom, or a pharmaceutically acceptable acid addition salt thereof.

The 1-benzyl-4-benzhydrylpiperazine derivative or an acid addition salt thereof is prepared by reductively condensing a benzaldehyde derivative with a fluorobenzhydrylpiperazine, or condensing a benzyl halide derivative with a fluorobenzhydrylpiperazine optionally in the presence of an acid acceptor, or condensing a benzylpiperazine with a fluorobenzhydryl halide derivative and, optionally converting the product to its acid addition salt.

The 1-benzyl-4-benzhydrylpiperazine derivative is useful for improving a cerebrovascular disease.

3 Claims, No Drawings

1-(2,3,4-TRI-METHOXYBENZYL)-4[BIS(4-FLUOROPHENYL)METHYL] PIPERAZINES ARE USEFUL FOR TREATING CEREBROVASCULAR DISEASE

This invention relates to novel piperazine derivatives, processes for production thereof, and pharmaceutical compositions comprising the piperazine derivatives as an active ingredient. More specifically, this invention relates to a 1-benzyl-4-benzhydrylpiperazine derivative represented by the following general formula (I)

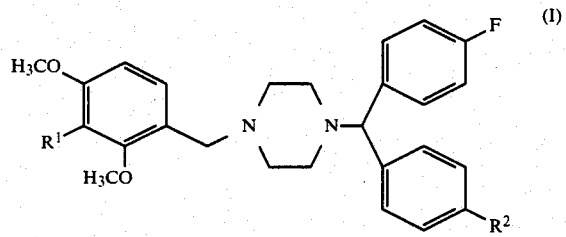

wherein
R$^1$ represents a hydrogen atom or a methoxy group, and
R$^2$ represents a hydrogen or fluorine atom,
or a pharmaceutically acceptable acid addition salt thereof, and an agent for improving cerebrovascular diseases of humans comprising the aforesaid compound as an active ingredient.

The cerebrovascular diseases can roughly be classified as intracranial hemorrhages such as intracerebral hemorrhage or subarachnoid hemorrhage, and cerebral infarctions such as cerebral thrombosis or cerebral embolus, transient ischemic attack, and hypertensive encephalopathy.

In these diseases, infarction of the brain parenchyma occurs owing to hemorrhage, thrombus, embolus, etc. within the brain, and leads to an insufficiency in glucose or oxygen which is an energy source for neuronal activity. This results in functional and organic disturbances in the ischemic area. Accordingly, drugs which supply glucose and oxygen to the ischemic area by increasing cerebral blood flow are effective for the treatment and prevention of these diseases.

Previously, various drugs such as cinnarizine, bencyclane fumarate, cyclandelate and cinepazide maleate have been clinically used for the purpose of treating these cerebrovascular diseases and subsequent complications, preventing relapse, improving their aftereffects, etc.

1-Benzyl-4-benzhydrylpiperazine derivatives and their therapeutic application have already been reported.

French Pat. No. M1538 discloses derivatives of 1-benzyl-4-benzhydrylpiperazine which have a 3,4-methylenedioxy group on the benzyl group and their application to vasodilation in coronary circulation. Particularly, the dihydrochloride of the compound of the following formula, commonly called Medibadine, is now clinically used.

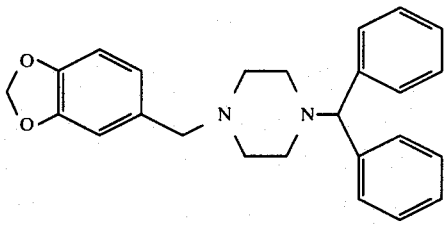

U.S. Pat. No. 3,868,377 discloses derivatives of 1-benzyl-4-benzhydrylpiperazine which are represented by the following formula and have a 4-hydroxyl group on the benzyl group and their suitability for the treatment of disturbances of cerebral blood flow.

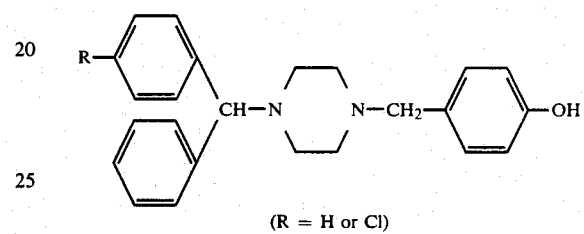

(R = H or Cl)

French Pat. No. 1303080 describes the compound of the following formula, but fails to disclose anything about its medical utility.

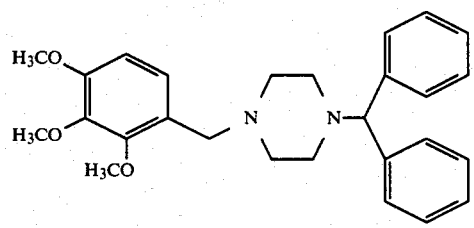

It is an object of this invention to provide a novel 1-benzyl-4-benzhydrylpiperazine derivative or its pharmaceutically acceptable acid addition salt.

Another object of this invention is to provide a novel 1-benzyl-4-benzhydrylpiperazine derivative or its pharmaceutically acceptable acid addition salt having an action of improving cerebrovascular diseases.

Still another object of this invention is to provide a process for producing a novel 1-benzyl-4-benzhydrylpiperazine derivative or its pharmaceutically acceptable acid addition salt.

These objects and advantages of this invention are achieved in accordance with this invention by a 1-benzyl-4-benzhydrylpiperazine derivative represented by the following general formula (I)

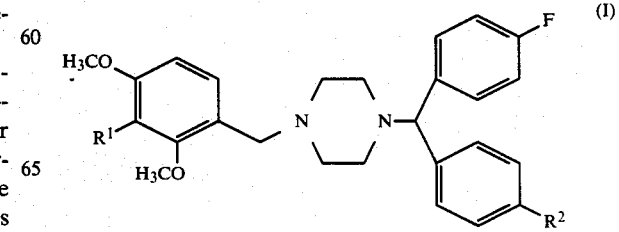

wherein
R[1] represents a hydrogen atom or a methoxy group, and
R[2] represents a hydrogen or fluorine atom,
or its pharmaceutically acceptable acid addition salt.

Specifically, the compounds of this invention are the following four compounds and their pharmaceutically acceptable acid addition salts. The acid addition salts include, for example, salts with inorganic acids such as hydrochloric acid, hydrobromic acid or sulfuric acid, and organic acids such as maleic acid, fumaric acid, succinic acid and citric acid.

1-(2,4-Dimethoxybenzyl)-4-(4-fluorobenzhydryl)-piperazine [the compound of formula (I) wherein R[1] and R[2] are H];

1-(2,4-dimethoxybenzyl)-4-[bis(4-fluorophenyl)-methyl]piperazine [the compound of formula (I) wherein R[1] is H and R[2] is F];

1-(2,3,4-trimethoxybenzyl)-4-(4-fluorobenzhydryl)piperazine [the compound of formula (I) wherein R[1] is OCH$_3$ and R[2] is H]; and 1-(2,3,4-trimethoxybenzyl)-4-[bis(4-fluorophenyl)-methyl]piperazine [the compound of formula (I) wherein R[1] is OCH$_3$ and R[2] is F].

By animal experiments, the compounds of this invention have been found to show an excellent action of increasing cerebral blood flow.

For example, in an experiment using dogs, the compounds of this invention have longer lasting effects and a stronger action of increasing cerebral blood flow than cinnarizine [cf. Ther. Hungarica, 21, 140 (1973)], a popular cerebrovascular disease improving agent in intravenous administration (see Test Example 1 given hereinbelow).

In addition, the compounds of this invention have been found to defend the thromboembolism-induced death of mice from simultaneous intravenous administration of adrenaline and collagen (see Test Example 2 given hereinbelow).

These facts indicate that the compounds of this invention are useful as agents for improving cerebrovascular diseases (including therapeutic and prophylactic drugs). As indicated hereinabove, one object of this invention is to provide such drugs.

The compounds of this invention can be produced, for example, by the following three processes (processes A, B and C).

Process A

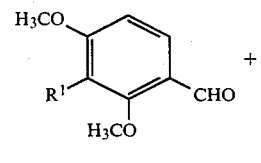

(II)

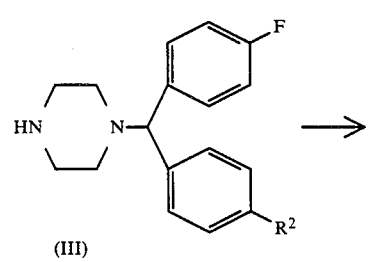

(III)

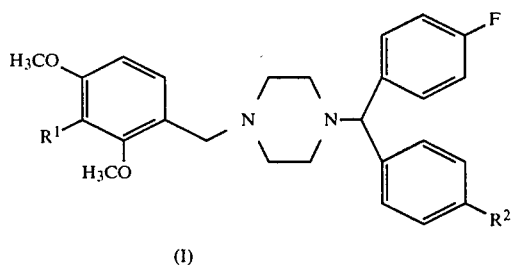

(I)

In the formulae, R[1] and R[2] are as defined hereinabove.

In process A, the compounds of this invention can be produced by reductively condensing a benzaldehyde derivative, namely 2,4-dimethoxy(or 2,3,4-trimethoxy)-benzaldehyde (II), with a fluorobenzhydrylpiperazine of general formula (III) as schematically shown above.

This reaction can be carried out under various conditions, but the following procedure is preferred because of its simplicity. Specifically, the benzaldehyde derivative of formula (II) and the fluorobenzhydrylpiperazine of formula (III) are melted by heating without using a solvent, and thereafter by adding formic acid, reductively condensed. In this case, the benzaldehyde of formula (II) is used in an equimolar or slightly excessive amount with respect to the piperazine of formula (III). Formic acid is used preferably in an amount of about 1 to 3 moles per mole of the piperazine of formula (III). The reductive condensation is carried out at a temperature of about 100° to 150° C. for a period of generally about 30 minutes to about 2 hours.

Process B

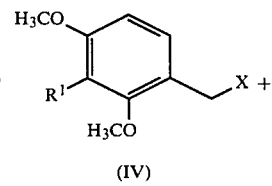

(IV)

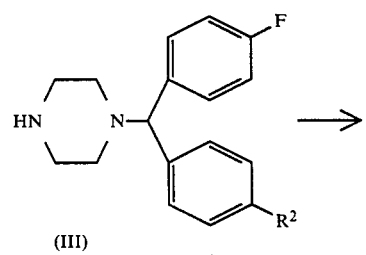

(III)

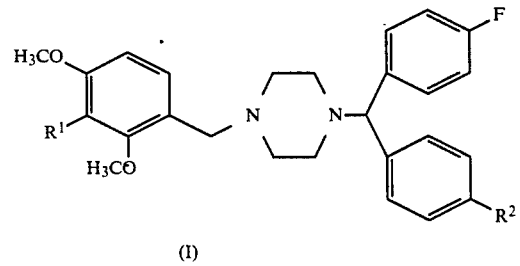

(I)

(R[1] and R[2] are as defined above, and X represents a halogen atom.)

In process B, a benzyl halide derivative, namely 2,3,4-trimethoxy(or 2,4-dimethoxy)benzyl halide (IV) is condensed with the piperazine derivative of formula (III) optionally in the presence of an acid acceptor in accordance with the above reaction scheme. The benzyl halide derivative (IV) is used in an equimolar or slightly excessive amount with respect to the piperazine (III). The reaction is carried out advantageously in an inert organic solvent. Examples of the solvent include aromatic hydrocarbons such as benzene and toluene, aliphatic alcohols such as methanol and ethanol, ketones such as acetone and methyl ethyl ketone, ethers such as tetrahydrofuran and dioxane, halogenated hydrocarbons such as chloroform and tetrachloroethane, dimethylformamide, and dimethyl sulfoxide.

The acid acceptor is preferably a nitrogen-containing basic compound, for example tertiary amines such as triethylamine and tributylamine, pyridine, picoline and quinoline.

The reaction temperature is from 50° C. to the boiling point of the solvent, and the reaction time is generally about 1 to 10 hours.

Process C

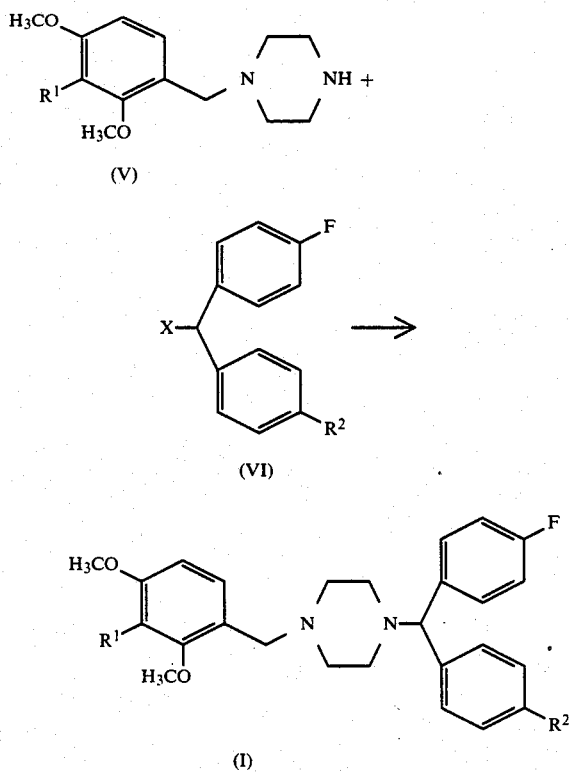

($R^1$, $R^2$ and X are as defined above.)

In process C, a benzylpiperazine, namely N-(2,3,4-trimethoxybenzyl)piperazine or N-(2,4-dimethoxybenzyl)piperazine (V), is condensed with the fluorobenzhydryl halide derivative of general formula (VI) optionally in the presence of an acid acceptor in accordance with the above scheme. The compound (VI) is used in an equimolar or slightly excessive amount with respect to the compound (V). The reaction is carried out advantageously in an inert organic solvent. The inert organic solvent and the acid acceptor may be the same as those described above with regard to process B. The reaction is performed by heating the reactants at 50° C. to the boiling point of the solvent. The reaction time is usually 6 to 24 hours.

The compounds of this invention obtained by the above processes are preferably converted to the aforesaid acid addition salts, and isolated from the reaction product and purified. As required, the salts may be converted into free bases or other various acid addition salts by a conventional method.

The following phamacological tests show the utility of the compounds of this invention.

TEST EXAMPLE 1

Activity of increasing cerebral blood flow:

(A) Test compounds 1-(2,4-Dimethoxybenzyl)-4-(4-fluorobenzhydryl)-piperazine fumarate (compound A of the invention)

1-(2,4-Dimethoxybenzyl)-4-[bis(4-fluorophenyl)-methyl]piperazine dihydrochloride dihydrate (compound B of the invention)

1-(2,3,4-Trimethoxybenzyl)-4-(4-fluorobenzhydryl)piperazine fumarate (compound C of the invention)

1-(2,3,4-Trimethoxybenzyl)-4-[bis(4-fluorophenyl)methyl]piperazine dihydrochloride (compound D of the invention)

1-(2,3,4-Trimethoxybenzyl)-4-benzhydrylpiperazine dihydrochloride monohydrate (comparative compound 1 described in French Pat. No. 130308) having the following formula

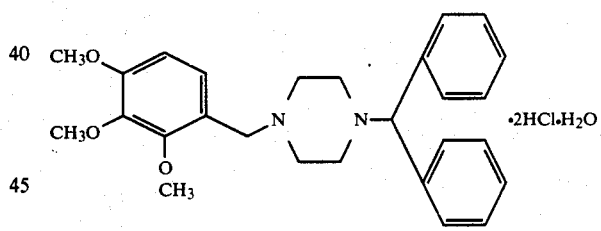

1-(3,4-Methylenedioxybenzyl)-4-benzhydrylpiperazine dihydrochloride (comparative compound 2, Medibazine dihydrochloride, described in French Pat. No. M1538) having the following formula

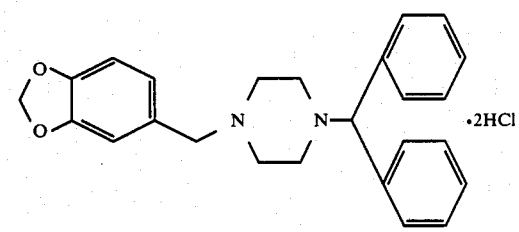

1-Cinnamyl-4-benzhydrylpiperazine [control compound, Cinnarizine, described in Ther. Hungaria, 21, 140 (1973)] having the following formula

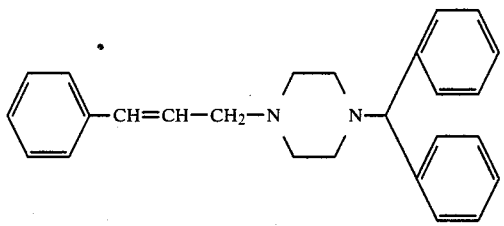

(B) Testing method

The activity of increasing cerebral blood flow was measured by using the amount of vertebral blood flow as an index. Mongrel dogs of either sex (body weight 11 to 18 kg; four per groups) were anesthetized with sodium pentobarbital (30 mg/kg, by intravenous injection), and the right vertebral artery was isolated from the surrounding tissues. A flow probe was attached to it and led to an electromagnetic flow meter (MFV-2100 made by Nihon Kohden Co., Ltd.). The amount of blood flow was periodically measured [see Meth and Find Exptl Clin Pharmacol, 3 (6), 397 (1981)].

Each of the test compounds was dissolved in a 2% tartaric acid solution containing 20% dimethylacetamide, and administered to the right femoral vein in a dose of 1 mg/kg.

(C) Results

Table 1 shows increases (%) in vertebral blood flow determined 0.5, 3, 5, 10 and 20 minutes after the administration of each test compound.

TABLE 1

| Test compound | Increase (%) in vertebral blood flow (mean ± standard error) Time (minutes) after administration | | | | |
|---|---|---|---|---|---|
| | 0.5 | 3 | 5 | 10 | 20 |
| Compound of the invention | | | | | |
| A | 80.1 ± 17.0 | 56.5 ± 15.0 | 39.1 ± 12.2 | 16.2 ± 5.4 | 11.3 ± 4.1 |
| B | 105.6 ± 3.9 | 85.8 ± 15.0 | 77.0 ± 15.6 | 47.5 ± 17.7 | 27.1 ± 13.4 |
| C | 76.7 ± 15.1 | 61.2 ± 14.9 | 50.6 ± 12.4 | 27.7 ± 6.3 | 16.4 ± 4.6 |
| D | 95.9 ± 14.5 | 102.6 ± 24.5 | 107.0 ± 23.9 | 87.0 ± 21.1 | 65.1 ± 15.3 |
| Comparative compound | | | | | |
| 1 | 75.3 ± 20.0 | 39.2 ± 15.3 | 25.6 ± 12.5 | 10.0 ± 5.3 | 5.0 ± 3.3 |
| 2 | 50.6 ± 13.2 | 13.5 ± 6.9 | 7.4 ± 4.9 | 2.5 ± 3.3 | 0.4 ± 2.2 |
| Cinnarizine | 65.6 ± 18.2 | 34.7 ± 15.6 | 17.0 ± 8.7 | 2.9 ± 3.8 | 0 |

TEST EXAMPLE 2

Activity of defending thromboembolism-induced death:

(A) Test compounds

The compounds A, B, C and D of the invention and the comparative compounds 1 and 2 were used.

(B) Testing method

Each of the test compounds was dissolved or suspended in a 1% gum arabic solution, and orally administered to ddY-strain male mice (body weight 18 to 25 g; five per group). One hour later, collagen (400 micrograms/kg) and adrenaline (50 micrograms/kg) were simultaneously injected into the tail vein, and the animals were observed for death. The dose required to defend death induced by collagen and adrenaline to an extent of 50% ($ED_{50}$) was determined by the probit method (see The Journal of Pharmacology and Experimental Therapeutics, Vol. 225, page 57, 1983).

(C) Results

The results are shown in Table 2.

TABLE 2

| Test compound | $ED_{50}$ (mg/kg) |
|---|---|
| Compound of the invention | |
| A | 29.6 |
| B | 24.6 |
| C | 32.7 |
| D | 7.7 |
| Comparative compound | |
| 1 | 55.4 |
| 2 | 44.7 |

TEST EXAMPLE 3

Acute toxicity:

ddY-strain male mice (body weight 18 to 22 g; five per group) were caused to fast 24 hours. Then, each of the compounds of this invention (A, B, C and D) was administered orally, and acute toxicity values ($LD_{50}$) were determined.

Each of the compounds was dissolved or suspended in a 2% tartaric acid solution containing 20% of dimethylacetamide, and orally administered to the animals. From the number of animals which died during seven days, the $LD_{50}$ values were calculated by using the Weil method. The results are shown in Table 3.

TABLE 3

| Test compound | $LD_{50}$ (mg/kg) |
|---|---|
| A | 300 |
| B | 225 |
| C | 650 |
| D | 300 |

The foregoing results of the pharmacological tests demonstrate that the compounds of this invention have longer lasting and stronger activities of increasing cerebral blood flow and defending thromboembolism-induced death than cinnarizine or the compounds described in the prior art documents (comparative compounds 1 and 2).

The compounds of this invention are administered to humans having cerebrovascular diseases in amounts effective for improving the cerebrovascular diseases.

Preferably, the compounds of this invention are orally administered to humans. For oral administration, the compounds of this invention, particularly their acid addition salts, are formed into tablets, granules, powders or capsules containing suitable amounts of granules or powders by a conventional method together with usual drug additives. Examples of the drug additives are vehicles such as lactose, synthetic aluminum silicate, glucose and mannitol, disintegrants such as carboxymethyl cellulose and sodium arginate, lubricants such as magnesium stearate and talc and binders such as corn starch and polyvinyl pyrrolidone.

The dose of the compounds of this invention varies depending upon the condition, body weight, age, etc. of the patient. Usually, the compound of the invention is administered either once or two or three times daily in a dose of about 0.01 to 1.0 mg/kg (calculated as free base) per adult per day.

EXAMPLE 1

Production of 1-(2,4-dimethoxybenzyl)-4-(4-fluorobenzhydryl)piperazine fumarate (process A):

2,4-Dimethoxybenzaldehyde (6.65 g; 40.0 millimoles) and 10.8 g (39.9 millimoles) of 4-fluorobenzhydrylpiperazine (see German OLS 1929330) were melted in an oil bath at 120° C., and 2.3 ml (61.0 millimoles) of formic acid was added dropwise. The mixture was stirred for 1 hour under heat, and then allowed to cool to room temperature. Then, 50 ml of an ethanol solution containing 5.0 g (43.1 millimoles) of fumaric acid was added, and the precipitated crystals were collected by filtration. Recrystallization of the crystals from ethanol gave 6.5 g (yield 30.4%) of 1-(2,4-dimethoxybenzyl)-4-(4-fluorobenzhydryl)piperazine fumarate as colorless crystals.

Melting point: 192° to 198° C. (decomp.)

NMR (DMSO-$d_6$, δ ppm): 2.1–2.8 (8H), 3.65 (2H, s), 3.74 (6H, s), 4.32 (1H, s), 6.52 (2H, s), 6.3–7.5 (12H, m), 8.32 (2H, broad s).

Elemental analysis for $C_{26}H_{29}FN_2O_2 \cdot C_4H_4O_4$: Calculated (%): C, 67.15; H, 6.20; N, 5.22. Found (%): C, 67.06; H, 6.11; N, 5.28.

EXAMPLE 2

Production of 1-(2,4-dimethoxybenzyl)-4-[bis(4-fluorophenyl)methyl]piperazine dihydrochloride (process A):

2,4-Dimethoxybenzaldehyde (6.7 g; 40.3 millimoles) and 11.5 g (39.9 millimoles) of bis(4-fluorophenyl)methylpiperazine were melted in an oil bath at 100° C., and 2.0 ml (53.0 millimoles) of formic acid was added dropwise. The mixture was stirred under heat for 30 minutes, and allowed to cool to room temperature. A mixture of 8 ml of conc. hydrochloric acid and 80 ml of ethanol was added, and the precipitated crystals were collected by filtration. Recrystallization of the crystals from ethanol gave 5.1 g (yield 25.0%) of 1-(2,4-dimethoxybenzyl)-4-[bis(4-fluorophenyl)methyl]piperazine dihydrochloride as colorless crystals.

Melting point: decomposed at about 160° C.

NMR (DMSO-$d_6$, δ ppm): 3.1–3.7 (8H), 3.76 (3H, s), 3.79 (3H, s), 4.24 (2H, s), 5.65 (1H, broad s), 6.4–8.1 (11H, m).

Elemental analysis for $C_{26}H_{28}F_2N_2O_2 \cdot 2HCl \cdot 2H_2O$: Calculated (%): C, 57.04; H, 6.26; N, 5.12. Found (%): C, 57.35; H, 6.18; N, 5.38.

By repeating the above procedure using fumaric acid instead of hydrochloric acid, 1-(2,4-dimethoxybenzyl)-4-[bis(4-fluorophenyl)methyl]piperazine fumarate was produced. The properties and elemental analysis values of this compound were as follows:

Form: colorless crystals

Melting point: 205°–208° C. (decomp.)

NMR (DMSO-$d_6$, δ ppm): 2.2–2.8 (8H), 3.62 (2H, s), 3.75 (6H, s), 4.36 (1H, s), 6.58 (2H, s), 6.3–7.6 (11H, m), 11.25 (2H, broad s).

Elemental analysis for $C_{26}H_{28}F_2N_2O_2 \cdot C_4H_4O_4$: Calculated (%): C, 64.97; H, 5.82; N, 5.05. Found (%): C, 64.97; H, 5.93; N, 5.19.

EXAMPLE 3

Production of 1-(2,3,4-trimethoxybenzyl)-4-(4-fluorobenzhydryl)piperazine fumarate (process A):

2,3,4-Trimethoxybenzaldehyde (7.85 g; 40.0 millimoles) and 10.8 g (39.9 millimoles) of 4-fluorobenzhydrylpiperazine (see German OLS 1929330) were melted in an oil bath at 120° C., and 2.3 ml (61.0 millimoles) of formic acid was added dropwise. The mixture was stirred under heat for 1 hour, and allowed to cool to room temperature. Then, 50 ml of an ethanol solution containing 5.0 g (43.1 millimoles) of fumaric acid was added, and the precipitated crystals were collected by filtration. Recrystallization of the crystals from ethanol gave 7.4 g (yield 32.7%) of 1-(2,3,4-trimethoxybenzyl)-4-(4-fluorobenzhydryl)piperazine fumarate as colorless crystals.

Melting point: 194° to 204° C. (decomp.)

NMR (DMSO-$d_6$, δ ppm): 2.2–2.8 (8H), 3.60 (2H, s), 3.70 (3H, s), 3.74 (6H, s), 4.30 (1H, s), 6.60 (2H, s), 6.7–7.6 (11H, m), 9.28 (2H, broad s).

Elemental analysis for $C_{27}H_{31}FN_2O_3 \cdot C_4H_4O_4$: Calculated (%): C, 65.71; H, 6.23; N, 4.94. Found (%): C, 65.43, H, 6.22; N, 5.01.

By repeating the above procedure using hydrochloric acid or oxalic acid instead of fumaric acid, 1-(2,3,4-trimethoxybenzyl)-4-(4-fluorobenzhydryl)piperazine dihydrochloride or oxalate were produced. The properties and elemental analysis values of these compounds are given below.

(1) Dihydrochloride

Form: colorless crystals

Melting point: 180°–187° C. (decomp.)

NMR (DMSO-$d_6$, δ ppm): 3.1–3.8 (8H), 3.80 (3H, s), 3.86 (3H, s), 3.94 (3H, s), 4.32 (2H, s), 5.76 (1H, broad s), 6.8–8.2 (11H, m).

Elemental analaysis for $C_{27}H_{31}FN_2O_3 \cdot 2HCl$: Calculated (%): C, 61.95; H, 6.35; N, 5.35. Found (%): C, 61.90; H, 6.41; N, 5.19.

(2) Oxalate

Form: colorless crystals

Melting point: 170°–173° C. (decomp.)

NMR (DMSO-$d_6$, δ ppm): 2.2–3.2 (8H), 3.78 (3H, s), 3.82 (3H, s), 3.86 (3H, s), 4.02 (2H, s), 4.44 (1H, s), 6.7–7.7 (11H, m), 9.62 (2H, broad s).

Elemental analysis for $C_{27}H_{31}FN_2O_3 \cdot C_2H_2O_4$: Calculated (%): C, 64.43; H, 6.15; N, 5.18. Found (%): C, 64.17; H, 6.20; N, 5.28.

EXAMPLE 4

Production of 1-(2,3,4-trimethoxybenzyl)-4-[bis(4-fluorophenyl)methyl]piperazine dihydrochloride (process A):

2,3,4-Trimethoxybenzaldehyde (42.1 g; 215 millimoles) and 61.9 g (215 millimoles) of bis(4-fluorophenyl)methylpiperazine were melted in an oil bath at 100° C., and 10 ml (265 millimoles) of formic acid was added dropwise. The mixture was stirred under heat for 30 minutes, and allowed to cool to room temperature. A mixture of 40 ml of conc. hydrochloric acid and 400 ml of ethanol was added, and the mixture was concentrated under reduced pressure. Ether was added, and the precipitated crystals were collected by filtration. Recrystallization of the crystals from ethanol-ether gave 55.5 g (yield 47.7%) of 1-(2,3,4-trimethoxybenzyl)-4-[bis(4-fluorophenyl)methyl]piperazine dihydrochloride as colorless crystals.

Melting point: decomposed at about 178° C.

NMR (DMSO-$d_6$, δ ppm): 3.0–3.7 (8H), 3.76 (3H, s), 3.82 (3H, s), 3.90 (3H, s), 4.30 (2H, s) 5.68 (1H, broad s), 6.7–8.2 (10H, m).

Elemental analysis for $C_{27}H_{30}F_2N_2O_3.2HCl$: Calculated (%): C, 59.89; H, 5.96; N, 5.17. Found (%): C, 59.89; H, 6.14; N, 5.22.

The above crystals (melting point: decomposed at about 178° C.) were further recrystallized from acetonitrile to give the captioned compound as colorless crystals having a melting point of 214° to 218° C. (decomp.).

By repeating the above procedure using fumaric acid instead of hydrochloric acid, 1-(2,3,4-trimethoxybenzyl)-4-[bis(4-fluorophenyl)methyl]piperazine fumarate was produced. The properties and elemental analysis values of this compound were as follows:

Form: colorless crystals
Melting point: 220°–224° C. (decomp.)
NMR (DMSO-$d_6$, δ ppm): 2.1–2.8 (8H), 3.52 (2H, s), 3.72 (3H, s), 3.77 (6H, s), 4.35 (1H, s), 6.60 (2H, s), 6.7–7.6 (10H, m), 11.30 (2H, broad s).

Elemental analysis for $C_{27}H_{30}F_2N_2O_3.C_4H_4O_4$: Calculated (%): C, 63.69; H, 5.86; N, 4.79. Found (%): C, 63.73; H, 5.93; N, 4.87.

EXAMPLE 5

Production of 1-(2,4-dimethoxybenzyl)-4-(4-fluorobenzhydryl)piperazine:

The 1-(2,4-dimethoxybenzyl)-4-(4-fluorobenzhydryl)piperazine fumarate obtained in Example 1 (2.0 g; 3.7 millimoles) was added to 20 ml of a 20% aqueous solution of sodium hydroxide. The resulting oily product was extracted with 20 ml of ethyl acetate. The ethyl acetate layer was dried over anhydrous magnesium sulfate. The solvent was evaporated under reduced pressure to give 1.1 g of 1-(2,4-dimethoxybenzyl)-4-(4-fluorobenzhydryl)piperazine as an oil.

NMR (CDCl$_3$, δ ppm): 2.2–2.7 (8H), 3.55 (2H, s), 3.80 (6H, s), 4.26 (1H, s), 6.4–7.6 (12H, m).

EXAMPLE 6

Production of 1-(2,4-dimethoxybenzyl)-4-[bis(4-fluorophenyl)methyl]piperazine:

The 1-(2,4-dimethoxybenzyl)-4-[bis(4-fluorophenyl)methyl]piperazine dihydrochloride dihydrate obtained in Example 2 (3.0 g; 5.9 millimoles) was added to 30 ml of a 20% aqueous solution of sodium hydroxide. The resulting oily product was extracted with 30 ml of ethyl acetate. The ethyl acetate layer was dried over anhydrous magnesium sulfate. The solvent was evaporated under reduced pressure to give 1.1 g of 1-(2,4-dimethoxybenzyl)-4-[bis(4-fluorophenyl)methyl]piperazine as an oil.

NMR (CDCl$_3$, δ ppm): 2.2–2.7 (8H), 3.48 (2H, s), 3.74 (6H, s), 4.17 (1H, s), 6.3–7.5 (11H, m).

EXAMPLE 7

Production of 1-(2,3,4-trimethoxybenzyl)-4-(4-fluorobenzhydryl)piperazine:

The 1-(2,3,4-trimethoxybenzyl)-4-(4-fluorobenzhydryl)piperazine fumarate obtained in Example 3 (3.0 g; 5.3 millimoles) was added to 30 ml of a 20% aqueous solution of sodium hydroxide. The resulting oily product was extracted with 30 ml of ethyl acetate. The ethyl acetate layer was dried over anhydrous magnesium sulfate. The solvent was evaporated under reduced pressure to give 1.6 g of 1-(2,3,4-trimethoxybenzyl)-4-(4-fluorobenzhydryl)-piperazine as an oil.

NMR (CDCl$_3$, δ ppm): 2.2–2.7 (8H), 3.50 (2H, s), 3.84 (3H, s), 3.88 (6H, s), 4.25 (1H, s), 6.5–7.6 (11H, m).

EXAMPLE 8

Production of 1-(2,3,4-trimethoxybenzyl)-4-[bis(4-fluorophenyl)methyl]piperazine:

The 1-(2,3,4-trimethoxybenzyl)-4-[bis(4-fluorophenyl)methyl]piperazine dihydrochloride obtained in Example 4 (20.0 g; 36.9 millimoles) was added to 100 ml of a 20% aqueous solution of sodium hydroxide. The resulting oily product was extracted with 100 ml of ethyl acetate. The ethyl acetate layer was dried over anhydrous magnesium sulfate. The solvent was evaporated under reduced pressure to give 11.1 g of 1-(2,3,4-trimethoxybenzyl)-4-[bis(4-fluorophenyl)methyl]piperazine as an oil.

NMR (CDCl$_3$, δ ppm): 2.2–2.7 (8H), 3.45 (2H, s), 3.79 (3H, s), 3.82 (6H, s), 4.17 (1H, s), 6.4–7.5 (10H, m).

EXAMPLE 9

Production of 1-(2,3,4-trimethoxybenzyl)-4-[bis(4-fluorophenyl)methyl]piperazine dihydrochloride (process B):

1.3 g (6.0 millimoles) of 2,3,4-trimethoxybenzyl chloride [see Monatsh., 95 (3), 942 (1964)], 1.7 g (5.9 millimoles) of bis(4-fluorophenyl)methylpiperazine and 1.2 ml (8.6 millimoles) of triethylamine were heated under reflux for 6 hours in 50 ml of benzene. The reaction mixture was allowed to cool to room temperature, washed with water, and dried over anhydrous magnesium sulfate. The solvent was evaporated under reduced pressure. A mixture of 2 ml of conc. hydrochloric acid and 20 ml of ethanol was added to the resulting oily product, and the mixture was concentrated under reduced pressure. Ether was added, and the precipitated crystals were collected by filtration. Recrystallization of the crystals from ethanol-ether gave 1.6 g of 1-(2,3,4-trimethoxybenzyl)-4-[bis(4-fluorophenyl)methyl]piperazine dihydrochloride as colorless crystals. The product showed the same property values as the compound obtained in Example 4.

EXAMPLE 10

Production of 1-(2,3,4-trimethoxybenzyl)-4-[bis(4-fluorophenyl)methyl]piperazine dihydrochloride (process C):

2.4 g (7.1 millimoles) of 2,3,4-trimethoxybenzylpiperazine dihydrochloride, 1.8 g (7.5 millimoles) of bis(4-fluorophenyl)methyl chloride [see J. Chem. Soc. Perkin II, 1051 (1977)] and 5.0 ml (36 millimoles) of triethylamine were heated under reflux for 9 hours in 80 ml of xylene. The reaction mixture was allowed to cool to room temprature, washed with water, and dried over anhydrous magnesium sulfate. The solvent was evaporated under reduced pressure. A mixture of 2 ml of conc. hydrochloric acid and 20 ml of ethanol was added to the resulting oily product, and the mixture was concentrated under reduced pressure. Ether was added, and the precipitated crystals were collected by filtration. Recrystallization of the crystals from ethanol-ether gave 0.85 g of 1-(2,3,4-trimethoxybenzyl)-4-[bis(4-fluorophenyl)methyl]piperazine dihydrochloride. The product showed the same property values as the compound obtained in Example 4.

EXAMPLE 11

Formulation example (tablets)
Recipe

| Ingredient | Amounts (parts by weight) |
| --- | --- |
| Compound D (*) | 5 |
| Lactose | 30 |
| Corn starch | 30 |
| Crystalline cellulose | 33 |
| Magnesium stearate | 2 |

(*): 1-(2,3,4-Trimethoxybenzyl)-4-[bis(4-fluorophenyl)methyl]piperazine dihydrochloride Operation Compound D of the invention, lactose and crystalline cellulose were weighed in the above-indicated amounts and uniformly mixed. To the resulting mixed powder was added a 5% aqueous solution of corn starch in an amount about one-fourth of the amount indicated above. The mixture was granulated by a wet granulating method to produce granules. Magnesium stearate and the remainder of corn starch were added to the granules. They were mixed and tableted into tablets each weighing 100 mg and containing 5 mg of the compound D of the invention.

EXAMPLE 12

Formulation example (capsules)
Recipe

| Ingredient | Amount (parts by weight) |
| --- | --- |
| Compound D of the invention | 1 |
| Lactose | 74 |
| Crystalline cellulsoe | 73 |
| Magnesium stearate | 2 |

Operation

The above ingredients were fully mixed to form a uniform mixed powder. The mixed powder was filled in capsules in an amount of 150 mg per capsule. Each capsule contained 1 mg of the compound D of the invention.

EXAMPLE 13

Formulation Example (granules)
Recipe

| Ingredient | Amount (parts by weight) |
| --- | --- |
| Compound D of the invention | 1 |
| Lactose | 50 |
| Corn starch | 49 |

Operation

The compound D of the invention and lactose were weighed in the above-indicated amounts, and corn starch was added as a 5% aqueous solution. The mixture was granulated by a wet granulating method to give granules which contained 1 mg of the compound D of this invention per 100 mg.

EXAMPLES 14–16

Tablets, capsules and granules each containing compound A of this invention, i.e. 1-(2,4-dimethoxybenzyl)-4-(4-fluorobenzhydryl)piperazine fumarate, as an active ingredient in the same way as in Examples 11 to 13 except that the compound A was used instead of the compound D of the invention.

EXAMPLES 17–19

Tablets, capsules and granules each containing compound B of this invention, i.e. 1-(2,4-dimethoxybenzyl)-4-[bis(4-fluorophenyl)methyl]piperazine dihydrochloride dihydrate, as an active ingredient in the same way as in Examples 11 to 13 except that the compound B was used instead of the compound D of the invention.

EXAMPLES 20–22

Tablets, capsules and granules each containing compound C of this invention, i.e. 1-(2,3,4-trimethoxybenzyl)-4-(4-fluorobenzyhydryl)piperazine fumarate, as an active ingredient in the same way as in Examples 11 to 13 except that the compound C was used instead of the compound D of the invention.

What is claimed is:

1. The compound 1-(2,3,4-tri-methoxybenzyl)-4-[bis(4-fluorophenyl)methyl]piperazine or a pharmaceutically acceptable acid addition salt thereof.

2. An agent for the treatment of a cerebrovascular disease which comprises an effective amount of the compound 1-(2,3,4-trimethoxybenzyl)-4-[bis(4-fluorophenyl)methyl]piperazine or a pharmaceutically acceptable acid addition salts thereof and a pharmaceutically acceptable carrier therefor.

3. A method for the treatment of a cerebrovascular disease in a human which comprises administering an amount, effective for the treatment of such disease, of 1-(2,3,4-trimethoxybenzyl)-4-[bis(4-fluorophenyl)methyl]piperazine or a pharmaceutically acceptable acid addition salt thereof to a human patient suffering from the cerebrovascular disease.

* * * * *